(12) United States Patent
Ullrich

(10) Patent No.: US 10,078,425 B2
(45) Date of Patent: Sep. 18, 2018

(54) STRONG AUTHENTICATION VIA DISTRIBUTED STATIONS

(71) Applicant: Meinhard Dieter Ullrich, Lexington, MA (US)

(72) Inventor: Meinhard Dieter Ullrich, Lexington, MA (US)

(73) Assignee: IMPRIVATA, INC., Lexington, MA (US)

( * ) Notice: Subject to any disclaimer, the term of this patent is extended or adjusted under 35 U.S.C. 154(b) by 69 days.

(21) Appl. No.: 14/945,671

(22) Filed: Nov. 19, 2015

(65) Prior Publication Data

US 2016/0142394 A1    May 19, 2016

Related U.S. Application Data

(60) Provisional application No. 62/081,820, filed on Nov. 19, 2014, provisional application No. 62/183,793, filed on Jun. 24, 2015.

(51) Int. Cl.

| | |
|---|---|
| *H04L 29/06* | (2006.01) |
| *G06F 3/0482* | (2013.01) |
| *G06F 3/0484* | (2013.01) |
| *H04L 29/08* | (2006.01) |
| *H04L 12/24* | (2006.01) |
| *H04W 4/04* | (2009.01) |
| *G06Q 50/22* | (2018.01) |
| *H04W 4/02* | (2018.01) |
| *H04W 64/00* | (2009.01) |
| *G16H 40/20* | (2018.01) |

(Continued)

(52) U.S. Cl.
CPC ........ *G06F 3/0482* (2013.01); *G06F 3/04842* (2013.01); *G06Q 50/22* (2013.01); *G16H 40/20* (2018.01); *H04L 41/22* (2013.01); *H04L 63/08* (2013.01); *H04L 67/12* (2013.01); *H04L 67/18* (2013.01); *H04L 67/22* (2013.01); *H04W 4/023* (2013.01); *H04W 4/043* (2013.01); *H04W 64/00* (2013.01); *H04W 12/06* (2013.01); *H04W 60/04* (2013.01)

(58) Field of Classification Search
CPC .. G06F 19/327; G06F 3/0482; G06F 3/04842; H04W 4/043; H04W 64/00; H04W 4/023; H04W 60/04; H04W 12/06; G06Q 50/22; H04L 63/08; H04L 67/22; H04L 41/22; H04L 67/18; H04L 67/12
See application file for complete search history.

(56) References Cited

U.S. PATENT DOCUMENTS

2010/0017608 A1*  1/2010  Larsen .................... H04L 41/12
                                                  713/168
2014/0129379 A1*  5/2014  Tryba .................. G06Q 30/0639
                                                   705/26.8

(Continued)

*Primary Examiner* — Mohammad A Siddiqi
(74) *Attorney, Agent, or Firm* — Morgan, Lewis & Bockius LLP

(57) ABSTRACT

In various embodiments, authentication stations are distributed within a facility, particularly in spaces where mobile devices are predominantly used—e.g., a hospital's emergency department. Each such station includes a series of authentication devices. Mobile device may run applications for locating the nearest such station and, in some embodiments, pair wirelessly with the station so that authentication thereon will accord a user access to the desired resource via a mobile device.

16 Claims, 3 Drawing Sheets

(51) Int. Cl.
*H04W 60/04* (2009.01)
*H04W 12/06* (2009.01)

(56) References Cited

U.S. PATENT DOCUMENTS

| | | | |
|---|---|---|---|
| 2014/0157381 A1* | 6/2014 | Disraeli | G06F 21/31 726/7 |
| 2014/0289790 A1* | 9/2014 | Wilson | G06Q 20/42 726/1 |
| 2015/0046969 A1* | 2/2015 | Abuelsaad | G06F 21/41 726/1 |
| 2015/0143485 A1* | 5/2015 | Tamura | G06F 21/6218 726/6 |
| 2015/0350140 A1* | 12/2015 | Garcia | H04L 51/043 715/753 |

* cited by examiner

STRONG AUTHENTICATION VIA DISTRIBUTED STATIONS

RELATED APPLICATION

This application claims the benefit of and priority to U.S. Provisional Patent Application Nos. 62/081,820, filed Nov. 19, 2014, and 62/183,793, filed Jun. 24, 2015, the entire disclosures of which are hereby incorporated by reference.

TECHNICAL FIELD

The invention relates generally to healthcare information technology, and in particular to systems and methods for managing secure access to data and applications.

BACKGROUND

In a busy healthcare environment, such as a hospital, clinicians roam frequently among patients, floors and buildings. Each time a clinician reaches a new location, she may require access to patient information or other medical data maintained by the facility (or elsewhere). That data may be accessed via a local, typically shared workstation, or via a handheld wireless device, such as a "smart phone" or tablet capable of hosting applications and establishing telecommunications, Internet and/or local intranet connections.

In particular, medical institutions from hospitals to physician practice groups to testing centers maintain diverse electronic medical records (EMR) systems, which collectively form the healthcare information backbone. EMR systems allow clinicians access to medical information maintained in various back-end systems. The typical workflow when a physician interacts with a patient involves first logging onto the computer system, then launching and logging into one or more EMR applications, selecting the right patient record, verifying that the record matches the patient, reviewing results (often from different sources), checking up on medical references, entering orders or prescriptions (e.g., using computerized physician order entry (CPOE) applications and ePrescribing), and/or charting patient progress. All of these activities may involve the same patient but different applications, and in some cases multiple separate applications for a single patient-specific activity.

Moreover, healthcare records are protected by strict privacy laws (such as the Health Insurance Portability and Accountability Act, or HIPAA), regulatory regimes, and institutional access policies. Accordingly, when a clinician moves from place to place, he may be required to log on to a new terminal or device, and because of data-access restrictions, the log-on procedure may involve cumbersome and/or multiple authentication modalities.

Indeed, for some highly sensitive transactions, a properly authenticated and logged-in user may be asked to re-authenticate using a stronger form of authentication. For example, the user may be asked to provide a fingerprint to a reader complying with Federal Information Processing Standard (FIPS) Publication 201-2, a one-time token or a smart card in order to satisfy an institutional policy or regulatory requirement. Particularly in an environment where nodes can be moved, and where users may access system resources using a personal wireless phone or tablet lacking sophisticated authentication modalities, the user may confront the need to search quickly, in stressful circumstances, for an available workstation with the appropriate authentication capability.

SUMMARY

In various embodiments, authentication stations are distributed within a facility, particularly in spaces where mobile devices are predominantly used—e.g., in a hospital's emergency department. Each such station includes a series of authentication devices, ideally spanning the range of possible modalities required of users, e.g., a FIPS-compliant fingerprint reader, a proximity-card reader, a smart-card reader, a vein reader, an iris scanner, a soft token application, etc. The mobile device may run an application ("app") for locating the nearest such station and, in some embodiments, pair wirelessly with the station so that authentication thereon will accord the user access to the desired resource via her mobile device. The authentication stations may be dedicated, stand-alone devices (e.g., deployed as kiosks). But in some embodiments, if a nearby workstation or other network node is not presently in use and has the needed authentication modality, the user may be guided to that node.

Accordingly, in a first aspect, the invention relates to a method of authentication and log-on to access a secure resource via a computer network. In various embodiments, the method comprises the steps of sending, via a computational device, an access request to a secure resource via a network; receiving, from the secure resource, a user authentication requirement involving an authentication modality; locating, via a mobile device, a nearest authentication station supporting the authentication modality; establishing wireless communication between the mobile device and the authentication station; obtaining, by the authentication station using the authentication modality, authentication credentials from a user; causing transmission of the authentication credentials to the authentication server; receiving, by the authentication station, an authentication confirmation from the authentication server and, via multiple-party communication among the mobile device, the authentication station, the computational device, and the secure resource, according access to the secure resource via the computational device.

The mobile device may be the computational device or may be different from, but in wireless communication with, the computational device. In various embodiments, the step of establishing wireless communication between the mobile device and the authentication station comprises claiming, by the mobile device, the authentication station until the authentication credentials have been received by the authentication station.

The multiple-party communication may comprise wirelessly communicating, by the authentication station via a secure link, the obtained authentication credentials to the wireless device, and wirelessly communicating, by the wireless device via a secure link, the authentication credentials to the authentication server. In one example of this flow the computational device is different from the wireless device, and the method further comprises wirelessly communicating, by the authentication station to the wireless device via a secure link, a token indicating acceptance of the obtained authentication credentials, and wirelessly communicating, by the wireless device via a secure link, the token to the computational device, whereby access to the secure resource is accorded to the computational device.

In some embodiments, the multiple-party communication comprises wirelessly communicating, by the wireless device via a secure link to the authentication server, the authentication credentials and session data identifying a session between an application running on the wireless device and the secure resource; and causing, by the authentication server, the computational device to be accorded access to the secure resource over the session.

The method may further comprise displaying, by the mobile device, a map showing a current location of the mobile device and a location of the authentication station.

In another aspect, the invention pertains to a system for facilitating authentication and log-on to access a secure resource via a computer network using an authentication modality. In various embodiments, the system comprises a network, a plurality of authentication stations, a computational device configured for requesting access to a secure resource via the network but lacking the authentication modality, and a mobile device comprising a processor and a memory storing an application. The application, when executed by the processor as a running process, causes the mobile device to identify a nearest one of the authentication stations supporting the authentication modality and establish wireless communication therewith. The identified authentication station is configured to (i) receive, using the authentication modality, authentication credentials from a user, (ii) transmit the authentication credentials to the authentication server, and (iii) receive an authentication confirmation from the authentication server. The mobile device, the authentication station, the computational device, and the secure resource, are configured for multiple-party communication whereby access is accorded to the secure resource via the computational device.

The mobile device may be the computational device or may be different from, but in wireless communication with, the computational device. The mobile device may be configured to wirelessly claim the identified authentication station until the authentication credentials have been received by the authentication station.

In some embodiments, the multiple-party communication comprises wireless communication by the authentication station of the obtained authentication credentials to the wireless device via a secure link, and wireless communication by the wireless device of the authentication credentials to the authentication server via a secure link. For example, the computational device may be different from the wireless device and the multiple-party communication may further comprise wireless communication by the authentication station to the wireless device via a secure link of a token indicating acceptance of the obtained authentication credentials. The wireless device is configured to use the token to obtain access to the secure resource.

In some embodiments, the multiple-party communication comprises wireless communication, by the wireless device via a secure link to the authentication server, of the authentication credentials and session data identifying a session between an application running on the wireless device and the secure resource, and the authentication server is configured to accord the computational device access to the secure resource over the session.

In some embodiments, the mobile device further comprises a display and a mapping application which, when executed by the processor as a running process, causes a map showing a current location of the mobile device and a location of the authentication station to appear on the display.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, routines, steps, or characteristics may be combined in any suitable manner in one or more examples of the technology. As used herein, the terms "approximately" and "substantially" mean ±10%, and in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
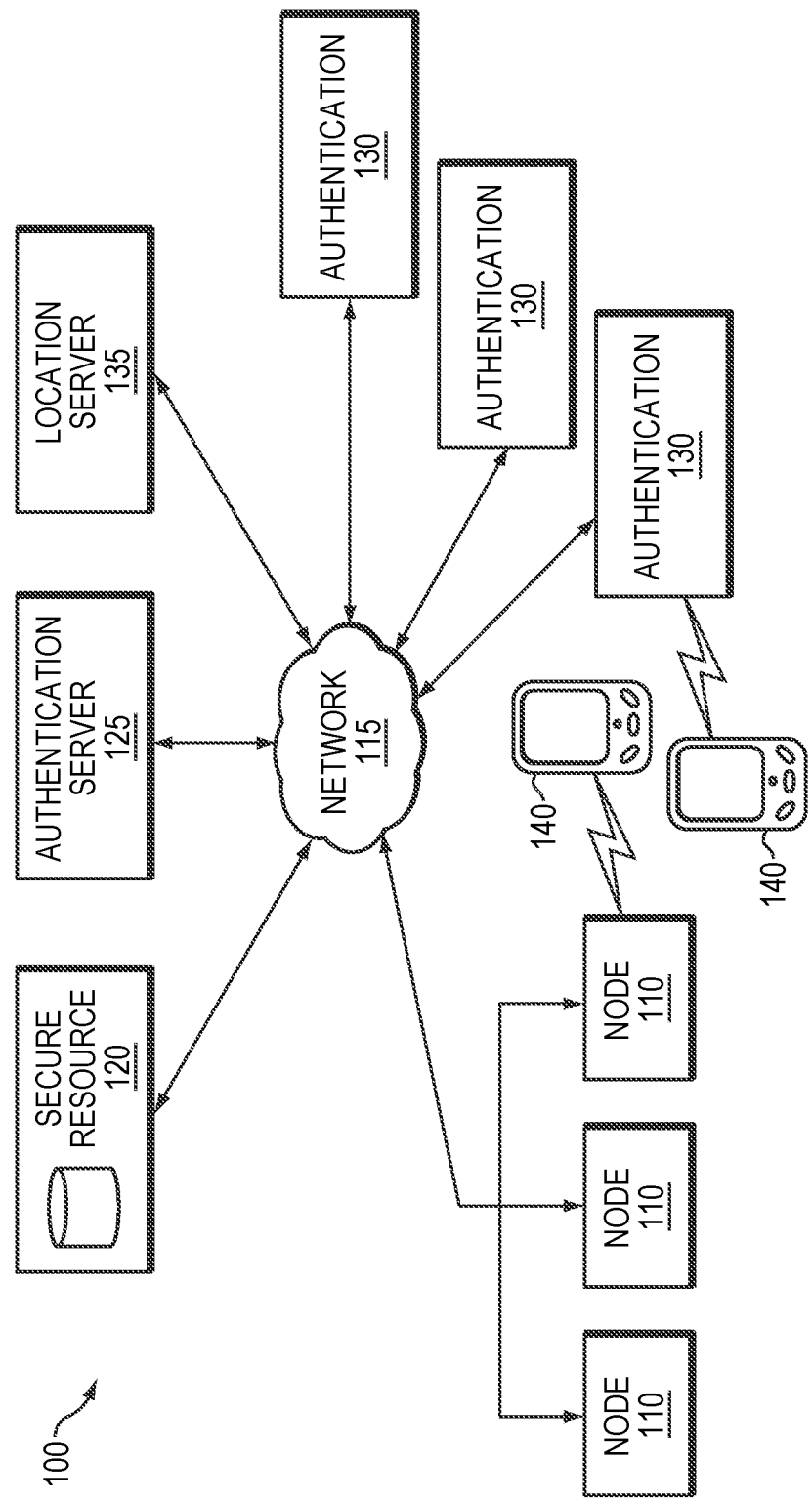
FIG. 1 schematically illustrates an institutional space including devices and servers in accordance with embodiments of the invention.

Refer first to FIG. 1, which illustrates a generalized system 100 in which embodiments of the invention may be utilized. For purposes of illustration, the system 100 is deployed in a healthcare environment, such as a hospital, and includes a series of devices 110 distributed about the institutional space. It should be understood, however, that the invention is amenable to deployment in any environment requiring ready access to secure resources by personnel who frequently change location.

Devices 100 may include workstations, thick or thin client devices, kiosks, and network-connected medical devices, and are herein referred to collectively as "nodes." In general, a node 110 is able to access, via a network 115, one or more secure data stores 120 or other resources that include sensitive information (e.g., EMR) of interest to clinicians. Access to secure resource 120, or at least to secure information stored thereon, is strictly controlled and requires a strong form of authentication. As used herein, the term "strong authentication" refers generally to any method of verifying the identity of a user or device and which is intrinsically stringent enough to guarantee, to a degree satisfying an institutional security policy, the identity of the individual seeking access. Often, strong authentication combines at least two mutually independent factors so that the compromise of one does not lead to the compromise of the other. Strong authentication typically includes one non-reusable element, such as a biometric indicium or one-time token, which cannot easily be reproduced or stolen from the Internet. For example, strong authentication may be provided by a FIPS-compliant fingerprint reader, a proximity-card reader, a smart-card reader, a vein reader, an iris scanner, or a soft token application.

Access to secure resource 120, as well as to other institutional resources, may be controlled by a conventional authentication server 125. Authentication server 125 implements the institution's security policy, which may require different tiers of authentication depending on the data to which the user seeks access; for example, a simple password log-in may be sufficient for access to routine applications, while strong authentication is required to sign a pharmaceutical order.

Because devices 110 may not have modalities supporting strong authentication, a series of authentication stations 130 are distributed within the institutional space. A location server 135 maintains a database relating the authentication stations 130 to their physical locations within the space. The stations 130 may be specialized, dedicated kiosks whose primary or sole purpose is to facilitate strong authentication by personnel seeking access to secure resources via devices that do not possess the requisite authentication modality. In addition, non-dedicated devices 110 may serve, either permanently or on an ad hoc basis, as authentication stations 130 if they possess an authentication modality required by a nearby user and are not currently in use. These devices 100 may be listed as authentication stations in the database of location server 135, but made available to users only when not currently in use; that is, location server 135 may maintain awareness of the use status of these devices.

It should be understood that the physical locations of servers 125, 135 can vary depending on system design. Multiple servers may reside on the same computer, and even separate machines need not reside in the institution's on-site data center; many facilities, for example, contract with a third party for authentication services delivered "in the cloud," i.e., remotely over the Internet or the public telecommunications infrastructure in a manner that is indistinguishable, to users, from a wholly local implementation. Accordingly, references herein to "servers" have no topological or device-level connotation; any functionally satisfactory deployment scheme, whether on a single or multiple machines wherever located, are within the scope of the present invention.

Furthermore, the term "network" is herein used broadly to connote wired or wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, Zigbee, IrDa, near-field communication (NFC), or other suitable protocol. Furthermore, components of the system may communicate through a combination of wired or wireless paths, and communication may involve both computer and telecommunications networks. For example, a user may establish communication with a server using a "smart phone" via a cellular carrier's network (e.g., authenticating herself to the server by voice recognition over a voice channel); alternatively, she may use the same smart phone to authenticate to the same server via the Internet, using TCP/IP over the carrier's switch network or via Wi-Fi and a computer network connected to the Internet.

Figure 2:
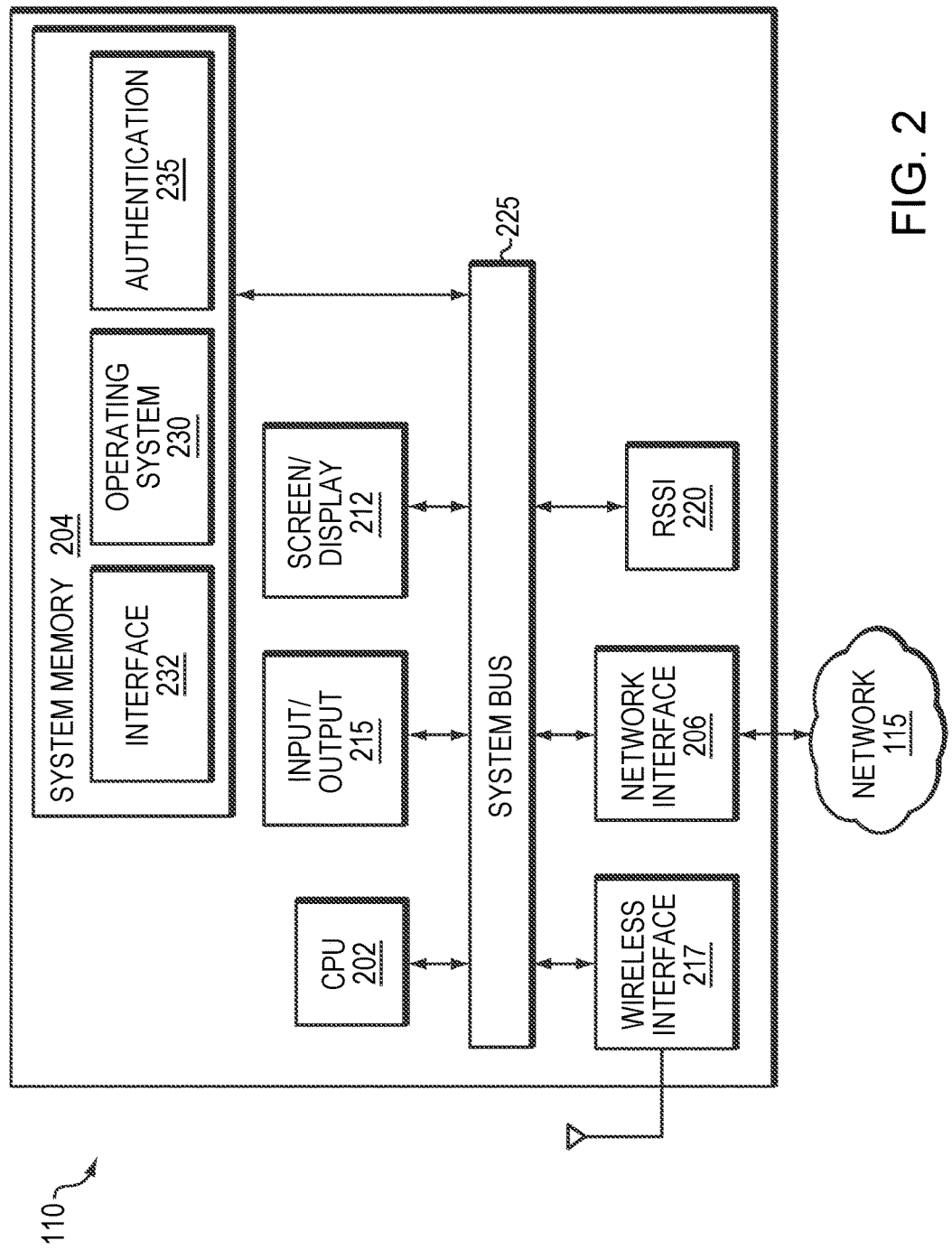
FIG. 2 schematically illustrates a node in accordance with embodiments of the invention.

FIG. 2 illustrates a representative node 110, which may be a workstation (e.g., a general-purpose personal computer running suitable software), a thick or thin client device, a kiosk, a network-connected medical device, or any other device with which clinicians and other users interact (e.g., a tablet or smartphone), and which may be moved from time to time within an institutional setting. Node 110 typically includes a processor 202 (e.g., a CPU microprocessor) and associated system memory 204, a network interface 206 (for connection to the institutional network 120 and/or the Internet), and, usually, one or more non-volatile digital storage elements (such as a hard disk, CD, DVD, USB memory key, etc.) and associated drives. Further, workstation 110 includes user input/output devices such as a display screen 212 and conventional tactile input devices 215 such as keyboard and mouse or touch pad. A wireless interface 217, which may be separate from or implemented within network interface 206, facilitates wireless communication with user mobile devices. In some embodiments, workstation 110 includes a received signal-strength indication (RSSI) circuit 220, which, again, may be implemented within or separate from wireless interface 217. The various components communicate with each other via one or more buses 225.

In use, processor 202 executes one or more computer programs (conceptually illustrated as program modules) stored in system memory 204. An operating system 230 (such as, e.g., MICROSOFT WINDOWS, UNIX, LINUX, iOS, or ANDROID) provides low-level system functions, such as file management, resource allocation, and routing of messages from and to hardware devices (such as I/O device(s) 215) and one or more higher-level user applications (such as EMR applications, office programs, a web browser, etc.) An interface 232 generates screen displays and receives user input via the input devices, e.g., by the user's typing on the keyboard, moving the mouse, or clicking with the mouse on a displayed control element. In some implementations, node 110 includes an authentication agent 235 that allows a user to obtain access to restricted data consistent with his privilege level and the security policies of the institution. Authentication agents are known in the art and described, for example, in U.S. Ser. No. 11/294,354, filed Dec. 5, 2005, the entire disclosure of which is hereby incorporated by reference, and may communicate with a remote authentication server that securely stores user credentials.

With renewed reference to FIG. 1, mobile wireless devices 140 are routinely carried by users and are employed in facilitating strong authentication. Mobile devices 140 may be "smart phones" or tablets with advanced computing ability that, generally, support bi-directional communication and data transfer using a mobile telecommunication network, and are capable of executing locally stored applications. Mobile devices include, for example, IPHONES (available from Apple Inc., Cupertino, California), BLACKBERRY devices (available from Research in Motion, Waterloo, Ontario, Canada), or any smart phones equipped with the ANDROID platform (available from Google Inc., Mountain View, California), tablets, such as the IPAD and KINDLE FIRE, and personal digital assistants (PDAs).

Figure 3:
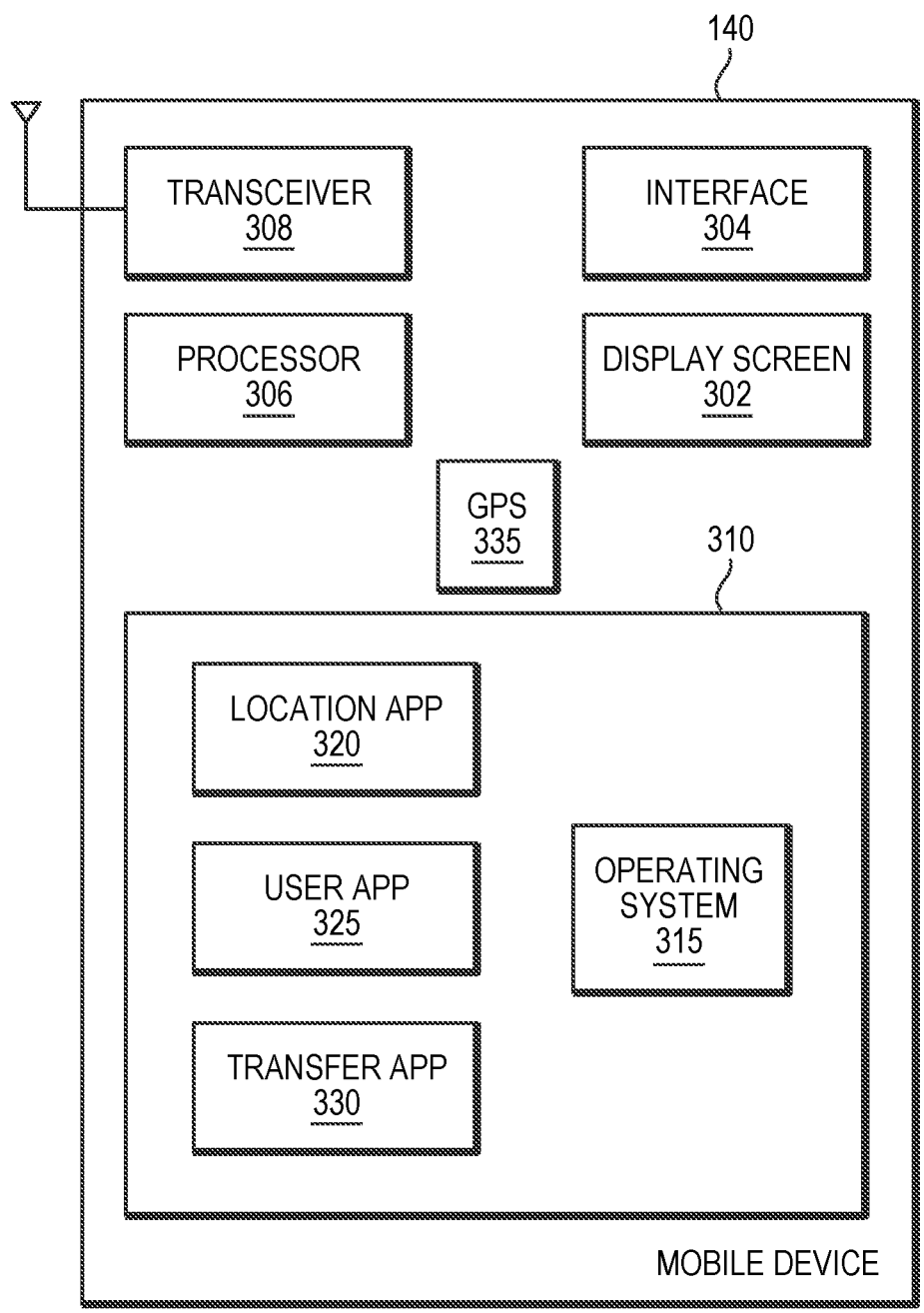
FIG. 3 schematically illustrates a mobile device in accordance with embodiments of the invention.

As shown in FIG. 3, a representative mobile device 140 includes a conventional display screen 302, a user interface 304, a computer processor 306, a transceiver 308, and a memory 310. The transceiver 308 may be a conventional component (e.g., a network interface or transceiver) designed to provide communications with a network, such as the Internet and/or any other land-based or wireless telecommunications network or system, and, through the network, with nodes 110 and authentication stations 140. Memory 310 includes an operating system 315, such as GOOGLE ANDROID, NOKIA SYMBIAN, BLACKBERRY RIM or MICROSOFT WINDOWS MOBILE, and one or more of three applications—a location app 320, a user app 325, and a transfer app 330. The wireless device 140 may also include a GPS receiver 335.

Location app 320 obtains the location of the nearest authentication station 130. This may be accomplished in any of various ways. Most simply, a map of authentication stations may be maintained at location server 135, which location app 320 contacts via a stored HTTP link that may be push-updated by server 135 as necessary. The HTTP link is modified to include the mobile device's location, e.g., using onboard GPS circuit 335 or an external location-tracking system such as "real-time location services" (RTLS), which monitors the changing locations of users (e.g., via wireless detection of tags worn by users and/or affixed to devices they carry); for example, location app 320 may use "deep linking" to communicate the GPS coordinates, or location server 135 may signal that it has already located the device 140 via RTLS. Server 135 returns the location of the nearest station 130, e.g., with a viewable floor map to enable the user to find it, and location app 320 causes the map to appear on display screen 302. Alternatively or in addition, location app 320 may initiate a Bluetooth device search process to determine whether any Bluetooth device within range is an authentication station 130, and if so, may cause mobile device 140 to establish a secure Bluetooth connection with the station. Authentication stations 130 may also be located using beacon technology that advertises (using, e.g., Bluetooth Low Energy) the services offered by specific nodes, including the availability of authentication devices 130 and proximity location services to indicate which mobile devices are close; for example, signals from multiple beacons maybe correlated to gain a more reliable fix on the location of the device. In this way, a workstation that is not currently and supports one or more strong authentication modalities may advertise its availability as an authentication station 130.

Transfer app 330 initiates wireless communication, via transceiver 308, with the nearest authentication station 130 when it comes into range—e.g., via a short-range wireless protocol. Transfer app 330 may execute a handshake protocol with the station, successful execution of which "claims" the authentication station for that mobile device until the authentication transaction has been completed (or until a timeout occurs). At this point, the authentication station 130 may establish an Internet Protocol (IP) connection with the mobile device, with further communication occurring via IP rather than the short-distance protocol for security purposes. The authentication credentials obtained from the user by the authentication station 130 may be provided to the mobile device 140 via the secure IP link (e.g., in encrypted format), and transfer app 330, in turn, may provide these credentials to the authentication server 125 governing access to the resource sought by the user. If the user is seeking access to the secure resource 120 via a user app 325 resident on the mobile device, the user will be free to proceed once the authentication credentials have been accepted. It should be noted that user app 325 may be one of several apps available on the device, and may or may not be exclusively associated with secure data; for example, user app 325 may be a dedicated EMR application that always requires strong authentication, or a data-retrieval or editing application that prompts for strong authentication only when the user seeks access to secure data.

In other embodiments, authentication station 130 may provide authentication credentials directly to an authentication server 125, bypassing mobile device 140 but using session information obtained therefrom so that authentication server 125 can match the incoming credentials with the access-seeking user and accord access permission to user app 325. By "session" is meant the interactive information interchange between mobile device 140 and the secure resource, e.g., a TCP session. "Session information" refers to data sufficiently identifying the session to allow authentication server to accord access thereover to a secure resource even though the user's authentication credentials arrived outside the session.

Alternatively, the user may seek access to a secure resource via a workstation 110, in which case mobile device 140 behaves as an intermediary. For example, when the user authenticates via a station 130, a token may be passed wirelessly from the station to transfer app 330 via a secure (i.e., encrypted) link, and when the user seeks access to the secure resource via a node 110, transfer app 330 passes the token to the node via another secure wireless link. (Secure wireless links are well known and readily established, using, for example, public-key cryptography and protocols such as Wi-Fi Protected Access.) Upon receiving the token, the node 110 supplies it to the secure resource as evidence of user authentication. In some cases, prior to transfer of the authentication token to the node 110, the node may pass its own token 110 to the mobile device 140 to establish that the node 110 is a trusted source (mitigating the concern that the requesting node might be a "man in the middle" or impostor asking for a credential). Transitive trust, in which trust passes from one device to another to the final destination, may be used to confirm the identity of the user.

Any suitable programming language may be used to implement without undue experimentation the functions described above, including those of apps 320, 325, 330. Illustratively, the programming language used may include assembly language, Ada, APL, Basic, C, C++, C*, COBOL, dBase, Forth, FORTRAN, Java, Modula-2, Pascal, Prolog, Python, RUM and/or JavaScript, for example. Further, it is not necessary that a single type of instruction or programming language be utilized in conjunction with the operation of the system and method of the invention. Rather, any number of different programming languages may be utilized as is necessary or desirable.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of authentication and log-on to access a secure resource via a computer network, the method comprising the steps of:

sending, via a computational device, an access request to a secure resource from a user via a network;

receiving, from the secure resource, a user authentication requirement involving an authentication modality, wherein the computational device does not support the authentication modality and cannot be solely utilized to satisfy the user authentication requirement;

locating, via a mobile device, a nearest authentication station supporting the authentication modality, wherein the nearest authentication station and the computational device are located at different locations;

establishing wireless communication between the mobile device and the authentication station;

obtaining, by the authentication station using the authentication modality, authentication credentials from the user, the user having traveled to the authentication station;

causing transmission of the authentication credentials to an authentication server different from the authentication station;

receiving, by the authentication station, an authentication confirmation from the authentication server and, via multiple-party communication among the mobile device, the authentication station, the computational device, and the secure resource, according access to the secure resource via the computational device.

2. The method of claim 1, wherein the mobile device is the computational device.

3. The method of claim 1, wherein the mobile device is different from, but in wireless communication with, the computational device.

4. The method of claim 1, wherein the step of establishing wireless communication between the mobile device and the authentication station comprises claiming, by the mobile device, the authentication station until the authentication credentials have been received by the authentication station.

5. The method of claim 1, wherein the multiple-party communication comprises:
   wirelessly communicating, by the authentication station via a secure link, the obtained authentication credentials to the wireless device; and
   wirelessly communicating, by the wireless device via a secure link, the authentication credentials to the authentication server.

6. The method of claim 5, wherein the computational device is different from the wireless device, and further comprising the steps of:
   wirelessly communicating, by the authentication station to the wireless device via a secure link, a token indicating acceptance of the obtained authentication credentials; and
   wirelessly communicating, by the wireless device via a secure link, the token to the computational device, whereby access to the secure resource is accorded to the computational device.

7. The method of claim 1, wherein the multiple-party communication comprises:
   wirelessly communicating, by the wireless device via a secure link to the authentication server, the authentication credentials and session data identifying a session between an application running on the wireless device and the secure resource; and
   causing, by the authentication server, the computational device to be accorded access to the secure resource over the session.

8. The method of claim 1, further comprising displaying, by the mobile device, a map showing a current location of the mobile device and a location of the authentication station.

9. A system for facilitating authentication and log-on to access a secure resource via a computer network using an authentication modality, the system comprising:
   a network;
   a plurality of authentication stations;
   an authentication server different from the authentication stations;
   a computational device configured for requesting access to a secure resource via the network but lacking the authentication modality, wherein the computational device is located at a location different from locations of the authentication stations; and
   a mobile device comprising a processor and a memory storing an application, the application, when executed by the processor as a running process, causing the mobile device to identify a nearest one of the authentication stations supporting the authentication modality and establish wireless communication therewith,
   wherein the identified authentication station is configured to (i) receive, using the authentication modality, authentication credentials from a user located at the authentication station, (ii) transmit the authentication credentials to the authentication server, and (iii) receive an authentication confirmation from the authentication server,
   and further wherein the mobile device, the authentication station, the computational device, and the secure resource, are configured for multiple-party communication whereby access is accorded to the secure resource via the computational device.

10. The system of claim 9, wherein the mobile device further comprises a display and a mapping application which, when executed by the processor as a running process, causes a map showing a current location of the mobile device and a location of the authentication station to appear on the display.

11. The system of claim 10, wherein the mobile device is the computational device.

12. The system of claim 10, wherein the mobile device is different from, but in wireless communication with, the computational device.

13. The system of claim 10, wherein the mobile device is configured to wirelessly claim the identified authentication station until the authentication credentials have been received by the authentication station.

14. The system of claim 10, wherein the multiple-party communication comprises:
   wireless communication by the authentication station of the obtained authentication credentials to the wireless device via a secure link, and
   wireless communication by the wireless device of the authentication credentials to the authentication server via a secure link.

15. The system of claim 14, wherein (i) the computational device is different from the wireless device and (ii) the multiple-party communication further comprises wireless communication by the authentication station to the wireless device via a secure link of a token indicating acceptance of the obtained authentication credentials, the wireless device being configured to use the token to obtain access to the secure resource.

16. The system of claim 10, wherein (i) the multiple-party communication comprises wireless communication, by the wireless device via a secure link to the authentication server, of the authentication credentials and session data identifying a session between an application running on the wireless device and the secure resource, and (ii) the authentication server is configured to accord the computational device access to the secure resource over the session.

* * * * *